(12) United States Patent
McKechnie

(10) Patent No.: US 8,535,653 B2
(45) Date of Patent: Sep. 17, 2013

(54) ARTICLES FOR THE RELEASE OR EMANATION OF VAPORS

(75) Inventor: Malcolm Tom McKechnie, Hull (GB)

(73) Assignee: Reckitt Benckiser (UK) Limited, Slough, Berkshire (GB)

( * ) Notice: Subject to any disclaimer, the term of this patent is extended or adjusted under 35 U.S.C. 154(b) by 523 days.

(21) Appl. No.: 10/534,133

(22) PCT Filed: Nov. 6, 2003

(86) PCT No.: PCT/GB03/04793
§ 371 (c)(1),
(2), (4) Date: Jun. 1, 2005

(87) PCT Pub. No.: WO2004/043501
PCT Pub. Date: May 27, 2004

(65) Prior Publication Data
US 2006/0140901 A1    Jun. 29, 2006

(30) Foreign Application Priority Data

Nov. 9, 2002    (GB) .................................. 0226203.8

(51) Int. Cl.
*A61L 9/04*    (2006.01)
(52) U.S. Cl.
USPC ........... 424/76.3; 424/76.4; 422/34; 514/944; 523/102

(58) Field of Classification Search
None
See application file for complete search history.

(56) References Cited

U.S. PATENT DOCUMENTS

| 3,865,108 | A |   | 2/1975  | Hartop ........................ 128/260 |
|-----------|---|---|---------|---------------------------------------|
| 4,002,173 | A |   | 1/1977  | Manning et al. ............... 128/296 |
| 4,207,893 | A |   | 6/1980  | Michaels ...................... 128/260 |
| 4,220,152 | A |   | 9/1980  | Dresback ...................... 128/260 |
| 4,293,095 | A |   | 10/1981 | Hamilton et al. ................ 239/35 |
| 4,327,725 | A |   | 5/1982  | Cortese et al. ................ 128/260 |
| 4,350,271 | A |   | 9/1982  | Eckenhoff ................. 222/386.5 |
| 5,034,222 | A |   | 7/1991  | Kellett et al. ................. 424/76.4 |
| 5,139,864 | A | * | 8/1992  | Lindauer .................... 428/304.4 |
| 6,129,771 | A |   | 10/2000 | Ficke et al. ...................... 44/275 |
| 2003/0091466 | A1 | * | 5/2003 | Benko et al. ...................... 422/5 |

FOREIGN PATENT DOCUMENTS

| EP | 0 348 970 A     | 1/1990  |
|----|------------------|---------|
| EP | 0890327 A1      | 1/1999  |
| EP | 1020177 A       | 7/2000  |
| FR | 2 253 536 A     | 7/1975  |
| GB | 2342581 A       | 4/2000  |
| WO | WO 94/23765 A1  | 10/1994 |

OTHER PUBLICATIONS

International Search Report dated Apr. 5, 2004 for Application PCT/GB03/04793.
International Preliminary Examination Report dated Feb. 4, 2005 for Application PCT/GB03/04793.
Combined Search and Examination Report from the Patent Office in Great Britain dated Apr. 29, 2003 for Application GB 0226203.8.
Combined Search and Examination Report from the Patent Office in Great Britain dated Jan. 29, 2002 for Application GB 0119229.3.
Search Report from the Patent Office in Great Britain dated Jan. 24, 2001 for Application GB 0017551.3.
Written Opinion dated Aug. 6, 2004 for Application PCT/GB03/04793.
Response dated Oct. 22, 2004 to Written Opinion dated Aug. 6, 2004 for Application PCT/GB03/04793.
Written Opinion dated Nov. 9, 2004 for Application PCT/GB03/04793.
Response dated Dec. 10, 2004 to Written Opinion dated Nov. 9, 2004 for Application PCT/GB03/04793.
Patent Abstracts of Japan; vol. 2003, No. 02; Feb. 5, 2003 -& JP 2002 291858 A (Kobayashi Phamaceut Co Ltd), Oct. 8, 2002; abstract.

* cited by examiner

*Primary Examiner* — Hasan Ahmed
(74) *Attorney, Agent, or Firm* — Norris McLaughlin & Marcus PA

(57) ABSTRACT

An article for sequential dispensing of vapors, notably evaporable fragrances, comprises separated first and second liquids (22, 24). Liquid (22) issues first. Its evaporation may be assisted by a wick (26). The simultaneous evaporation of the second liquid is prevented by an intermediate liquid phase (20). As liquid (22) issues the liquid levels change and there comes a point at which the intermediate phase can no longer prevent the second liquid (24) from flowing past it, to the region from which it can be evaporated. Solids, especially gels, may be employed instead of liquids (22, 24).

9 Claims, 3 Drawing Sheets

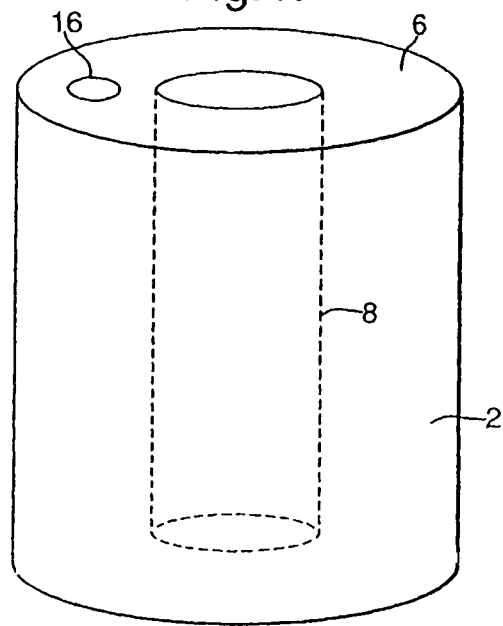
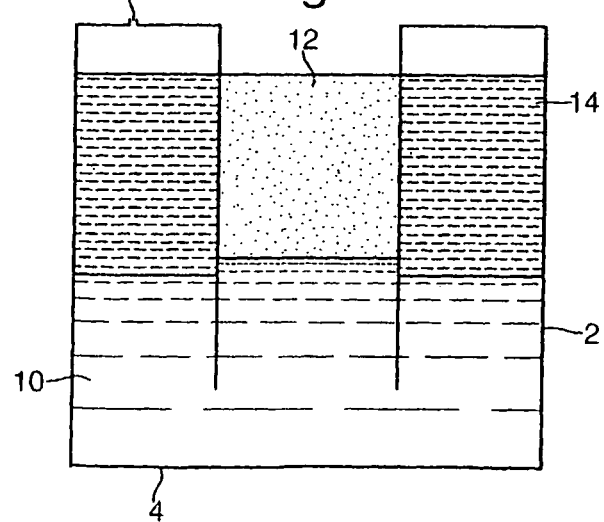

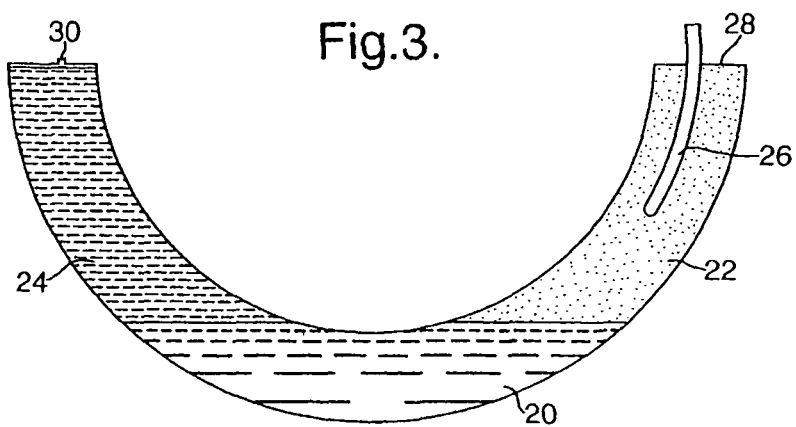
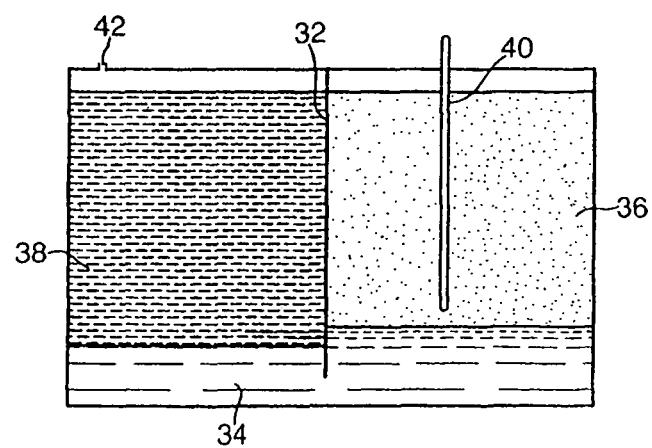

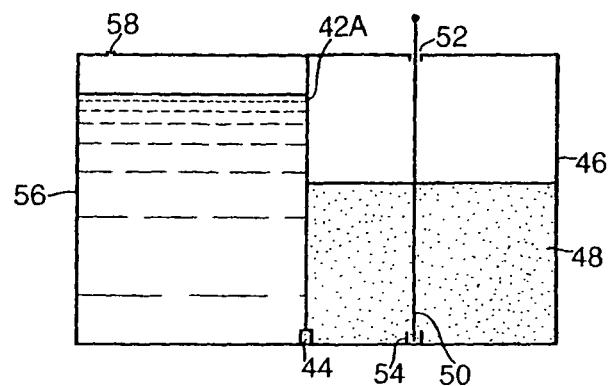
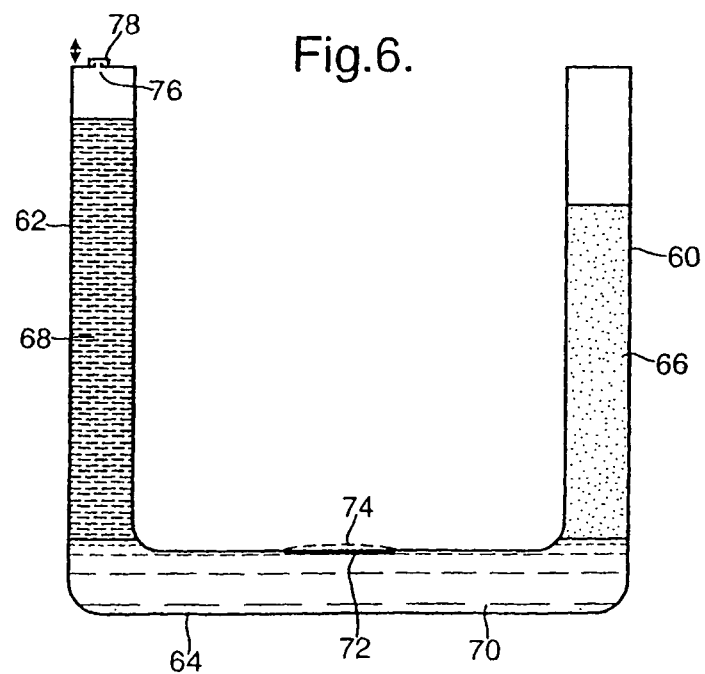

ARTICLES FOR THE RELEASE OR EMANATION OF VAPORS

This invention relates to articles for the release of vapours.

It would be desirable to provide one article which could emit more than one vapour, for example fragrance or other active agent, automatically and in a sequential manner.

In accordance with a first aspect of the present invention there is provided an article for the release of a plurality of vapours, the article containing:
a first liquid or solid phase comprising a first vaporisable agent;
a second liquid or solid phase comprising a second vaporisable agent;
and a third phase which constitutes a barrier between the first and second phases;
wherein the first and second phases are such that if placed in contact with each other one phase or one or more component thereof would mix or migrate into the other phase;
and wherein the article is such that, in use, initially vaporisation of the first agent commences, and subsequently vaporisation of the second agent commences, the commencement of vaporisation of the second agent being delayed by the third phase.

The article of the present invention is useful when it is wished to release different vapours, or a different blend of vapours, at different times. When the vapours are fragrances this may help to avoid "nasal attenuation" (anosmia) of a user—the process by which the user becomes so accustomed to a single fragrance that he or she no longer perceives it. When the vapours are insecticides, insect repellents or miticides the release of different vaporised active agents, at different times, may increase the effectiveness by challenging the insects or mites with a different or more complex active agent, and may assist in reducing the onset of resistance.

The invention is useful in situations where the first phase and the second phase could mix or migrate into each other, if placed in contact together. The third phase performs the function of a barrier, preventing this. Clearly, in situations in which the first phase and the second phase remain entirely separate from each other even when in contact with each other, there would be no need for a barrier; the present invention would be of no benefit in this situation.

On the other hand, the degree of mixing or migration of the first and second phases does not have to be very great for the placement together to be undesirable; accordingly in such embodiments a third phase acting as a barrier is required.

The present invention is highly applicable to situations in which the first and second phases are liquids which are miscible with each other. However it is also applicable to situations in which the first liquid is slightly miscible in the second liquid; and/or in which the second liquid is slightly miscible in the first liquid.

Similar considerations apply when one of the first and second phases is a solid, for example a gel, and the other of the first and second phases is a liquid. If such phases are placed together one can have the situation that the liquid phase is absorbed entirely into the solid phase; or the solid phase is dissolved entirely in the liquid phase. The result could be a single phase—probably a liquid due to break up of the gel. As an alternative, there could remain two distinct phases but with the composition of one or both phases modified by mixing or migration of one into the other. In all such embodiments the provision of a barrier layer to provide the controlled sequential release of vapours is usefully employed, in accordance with the invention.

In situations where the first and second phases are both solids, for example gels, it may be the case that one solid, or one or more component of it, mixes or migrates into the other solid. This may happen continuously due to the process of diffusion. Alternatively or additionally it may arise as a result of the manufacture, as one solid is laid on top of the other solid. In such embodiments a barrier is provided in the form of a third phase, to prevent premature mixing or migration.

Preferably an article in accordance with the present invention provides automatic release of a desired vapour.

Preferably the article does not have electrical connections.

Preferably there is no consumer intervention once the operation is started. Furthermore, operation is typically started by exposing the first phase to the atmosphere, for example by the simple measure of removing a cap or seal and in certain embodiments, opening an aperture to provide an air vent into an otherwise closed space in communication with the second phase.

The first evaporable agent may be released into the air by evaporation from the first phase. This may occur, for example, when the first phase is a non-volatile gel into which the evaporable agent is releasably absorbed.

Preferably, however, the first phase is itself evaporated, thereby releasing the first evaporable agent.

The second evaporable agent may be released into the air by evaporation from the second phase. This may occur, for example, when the second phase is a non-volatile gel into which the second evaporable agent is releasably absorbed.

Preferably, however, the second phase itself evaporates, thereby releasing the second evaporable agent.

In the following passages the context will make clear whether we are discussing an embodiment in which an evaporable agent is released from its associated phase or one in which it evaporates with it.

Preferred articles of the invention are fragrancing articles. Suitably the first liquid phase is an evaporable fragrance. Preferably the second phase is an evaporable fragrance.

In other embodiments the articles may be insecticidal, insect-repelling, miticidal or anti-allergenic. At least one of the phases may contain an appropriate evaporable agent for such a use.

If wished the third phase may contain an evaporable agent as mentioned above; preferably a fragrance.

The third phase may be an aqueous phase (including a hydrogel). It may be a liquid phase, for example water. It may be a solid liquid-rich, preferably water-rich, phase. It is preferably a hydrogel. When the third phase is an aqueous phase the first and second phases are both phases substantially immiscible in water, under ambient conditions.

When the phases are liquids the density of the third phase exceeds the densities of the first and second phases.

The first phase could be a solid which is not a gel, for example an impregnated wax which has a wick and is burnt in the manner of a candle.

The first phase could be an oil which is heated, for example by burning a wick therein.

In other embodiments the first and second phases could be aqueous phases and the third phase could be a gel. Suitably this could be a non-aqueous phase, preferably a hydrophobic gel. However, it could be a water-containing gel provided that it keeps the first and second phases apart.

When the third phase is a gel, where it contacts the article it may in preferred embodiments be bound to it. In other embodiments it need not be bound to it, provided that it can keep the first and second phases apart.

In embodiments which employ a hydrogel for one or more of the phases, the hydrogel suitably includes a hydrogel-forming polymeric material, optionally of plant, animal or synthetic origin. The material interacts with water by absorbing the water and swelling or expanding to an equilibrium state. The hydrogel preferably exhibits the ability to retain a significant fraction of imbibed water in its polymeric molecular structure.

Preferably the hydrogel is a gel polymer that can swell or expand to a very high degree; for example it can have a 2- to 50-fold volume increase. A suitable gel polymer is a swellable, hydrophilic polymer (or an osmopolymer) which is optionally either non-cross-linked or lightly cross-linked. The cross-links can be covalent, ionic or hydrogen bonds so that the polymer possesses the ability to swell in the presence of water but does not dissolve in the water.

A hydrogel suitable for use is, for example, a poly(hydroxyalkylmethacrylate) having a molecular weight from 5,000 to 5,000,000; poly(vinylpyrrolidone) having molecular weight from 10,000 to 360,000; an anionic and/or cationic hydrogel; a poly(electrolyte) complex; poly(vinyl alcohol) having a low acetate residual; a mixture of agar and carboxymethyl cellulose; a composition comprising methyl cellulose mixed with a sparingly cross-linked agar; a copolymer produced by a dispersion of finely divided copolymer of maleic anhydride with styrene, ethylene, propylene or isobutylene; an N-vinyl lactam polymer; a sodium salt of carboxymethyl cellulose; a pectin having a molecular weight ranging from 30,000 to 300,000; a polysaccharide such as agar, acacia, karaya, tragacenth, carrageenans, algins and guar; an acidic carboxy polymer or its salt derivative such as one sold under the trade name CARBOPOL; a polyacrylamide; an indene maleic anhydride polymer; a polyacrylic acid having a molecular weight of 80,000 to 200,000 such as one sold under the trade name GOOD-RITE; a polyethylene oxide polymer having a molecular weight of 100,000 to 5,000,000 such as one sold under the trade name GOOD-RITE; a starch graft copolymer; an acrylate polymer with water absorbability of about 400 times its original weight such as one sold under the trade name AQUA-KEEP; a diester of polyglucan; a mixture of cross-linked poly(vinyl alcohol) and poly(N-vinyl 2-pyrrolidone); and poly(ethylene glycol) having a molecular weight of 4,000 to 100,000.

Other suitable hydrogels are disclosed in U.S. Pat. Nos. 3,865,108, 4,002,173, 4,207,893, 4,220,152, 4,327,725 and 4,350,271, and in Scott et al, Handbook of Common Polymers, CRC Press, Cleveland, Ohio (1971); all of which are incorporated herein by reference.

Another type of gel which is useful for one or more of the phases is a crosslinked polymeric gel. Especially suitable is a gel comprising a maleinised polybutadiene and an amine crosslinking agent, suitably a tri-amine or, especially, a di-amine compound; and preferably having the property that when exposed to air it shrinks. Such a gel is especially useful as the third phase, selected to shrink sufficiently, when exposed to air, for the gel to be breached.

Preferably the article, especially one employing liquid phases, has an emanating device, for example a wick, located to assist the release of at least the first evaporable agent. A wick, preferably the same wick, may also assist the release of the second evaporable agent.

In one embodiment employing evaporable liquid phases the article is generally U-shaped, with the first and second phases initially in the respective limbs, and with the third phase in the bottom region of the article, between the limbs. The first phase is released from the article at the top of one limb. The top region of the other limb is provided with an air vent, which is sufficiently small that the release of a second active agent is negligible. The air vent may be covered with a gas-permeable liquid-impermeable membrane. As the first phase is released from the article the interface between the second phase and the third phase adopts a progressively lower position, and there comes a time when second phase can flow from its limb, through the bottom region of the article, into the other limb. At this point the second phase can start to issue from the article.

In an alternative embodiment employing liquid phases an article in accordance with the invention comprises a bottom wall, and a side wall (if cylindrical) or side walls (if not). At the top of the side wall or walls there is an inwardly extending top wall, which surrounds an aperture. Extending downwardly from the inner edge of the top wall is a central tubular body, whose bottom end is open. The tubular body constitutes a kind of well. The second phase is located in the space between the tubular body and the side wall, or walls, of the article. The second phase is located within the tubular body. The third phase is located at the bottom of the article, underneath the first phase and the second phase. The amount of the third phase present is such that it, in conjunction with the wall of the tubular body, keeps separate the first phase and the second phase. However as the first phase issues the liquid level changes and there comes a point where the interface between the second phase and the third phase has moved sufficiently low, that the second phase can flow under the bottom edge of the wall which defines the tubular body, and into the tubular body. From the tubular body it can issue from the article, for example by evaporation.

In another embodiment an article in accordance with the invention is in the form of a box-like enclosure, having a partition wall extending from its top wall to a position somewhat spaced from its bottom wall. The third phase is located at the bottom of the article, and the lower edge of the partition wall is immersed in it. The first phase is located above the third phase on one side of the partition wall. The second phase is located above the third phase on the other side of the partition wall. The first phase may be associated with suitable delivery means, for example a wick extending through the top wall. The volume above the second phase may be vented by, for example, an upper pin hole.

The movement of the second phase to a position from which it can issue from the article may be assisted by selection of a gel for the third phase, having a tendency to shrink over time and/or when exposed to air.

In certain embodiments the third phase is a gel which is in fixed position within the article, being bound to surfaces of the article. When the first phase has issued the third phase is exposed to air and can shrink. After a certain degree of shrinkage a liquid second phase can flow through or around the third phase, and the second phase may then evaporate from the article. In related embodiments the shrinkage of the third phase could be initiated prematurely by the user. For example a patch may be provided, which a user may remove in order to expose the third phase to the air, preferably through a gas-permeable liquid-impermeable membrane, for example if an early change of fragrance is desired. This may be readily achieved when the article is generally U-shaped, having a gel which constitutes the third phase. The patch can be provided in an upper part of the link between the limbs.

Preferably the first and second phases are of different colour. Preferably the third phase is of a different colour again. When the first and second phases are liquids and the article is designed such that when the second phase passes the third phase there is some of the first phase left, the mixing of the second phase and the remaining first phase produces a different colour again. This may be a mixing effect or may be a substantive chemical effect.

In all embodiments operation of the article may employ a heat source (for example a flame, indirect or direct—for example by burning a wick, or an electrical heater) and/or a fan.

In accordance with a second aspect of the present invention there is provided a method of releasing at least two vapours, the commencement of the release of a first vapour preceding the commencement of the release of a second vapour, using an article in accordance with the first aspect of the present invention.

The invention will now be further described, by way of example, with reference to the accompanying drawings in which:

FIG. 1 is a perspective view of a first article in accordance with the present invention;

FIG. 2 is a schematic cross-sectional view of the article of FIG. 1;

FIG. 3 is a schematic sectional view of a second article in accordance with the present invention;

FIG. 4 is a schematic view of a third article in accordance with the present invention.

FIG. 5 is a schematic view of a fourth article in accordance with the present invention; and FIG. 6 is a schematic view of a fifth article in accordance with the present invention.

The article shown in FIGS. 1 and 2 has a cylindrical side wall 2 and a circular base wall 4. It has an annular top wall 6 joined with the side wall. The inner periphery of the annular top wall 6 is connected to a cylindrical inner wall 8, co-axial with the side wall 2, and forming a well, extending into the article. The well is open at its top end and at its bottom end. Its bottom end terminates a little way above the bottom wall 4 of the article.

With reference to FIG. 2, water 10 fills the bottom section of the article contains tinted water 10, and the bottom region of the inner wall 8 forming the well is immersed in the water. Water 10 is thus located in the bottom region of the well, and in the bottom part of the annular region around the well. Above the water within the well is a first hydrophobic phase 12, comprising a fragrance, and coloured. Above the water 10 within the annular section is a second hydrophobic phase 14, comprising a different fragrance, and differently coloured. The first and second hydrophobic phases are substantially immiscible with the water.

The top wall 6 of the article has a peel-off venting film 16. On peeling off the venting film 16 a very small vent hole 18 is exposed. In some embodiments this may be covered by a gas-permeable liquid-impermeable membrane.

In use, after the venting film 16 has been peeled off to expose the vent hole 18, and a peel-off sticker (not shown) over the top of the well is removed, the first phase 12 is free to evaporate, and release its fragrance. As it evaporates all the liquid levels adjust. The second phase 14 moves lower, within the annular region. Evaporation of the first phase 12 continues and a point is reached when the second phase can bleed under the bottom edge of the inner wall 8, and into the well. It rises through the water to form a separate phase on the top of the water. As it evaporates, more of the second phase can bleed into the well, and then be evaporated. The vent hole 18 is so small that the passage through it of evaporated second phase is negligible.

The geometry of the article and/or amounts of the phases may if desired be arranged such that substantially at the point where the first phase has been entirely removed by evaporation, the second phase can start to bleed into the well.

In the second embodiment shown in FIG. 3 the article is a generally U-shaped tube. At the bottom of the "U" a water-swollen carrageenan hydrogel 20 is located. Above the hydrogel, and within the right-hand limb, as viewed, there is a first hydrophobic phase 22 comprising a first fragrance. Above the hydrogel, and within the left-hand limb, there is a second hydrophobic phase 24 comprising a second fragrance. The three phases are all coloured, differently.

Within the right hand limb there is a wick 26. The wick 26 has a major portion that is located within the first phase, above the initial level of the interface between the first and second phases, and a minor portion projecting beyond the limb, and through an opening in the end wall 28 of the limb. If wished a wick may be employed extending to the bottom of the tube, in order to obtain wick-assisted emanation throughout the life of the product.

The left-hand limb has a tiny vent hole 30 in its end wall. The vent hole 30 may be exposed by removal of a peel-off venting film, as described for FIGS. 1 and 2.

It is important to note that at the commencement of use there is sufficient hydrogel 20 for the tube to be entirely occluded, in its lower region. The hydrogel is not bound to the wall of the tube.

In use, once a cap (not shown) has been removed from the right limb, in order to expose the wick, and the venting film has been removed from the left limb, the first fragrance issues from the article by evaporation from the exposed portion of the wick 26. As evaporation continues the levels of the interfaces between the hydrogel 20 and the hydrophobic phases adjust. After substantial or complete evaporation of the first phase, the second phase is free to flow into the first limb, from which it then evaporates.

An alternative embodiment is the same as that described with reference to FIG. 3, except that the hydrogel is bound to the wall of the tube. As the first phase evaporates there is no change in the levels of the interfaces between phases. After complete evaporation of the first phase the hydrogel is exposed to air and shrinks, by evaporation of water. After a certain degree of shrinkage the second phase can burst through or past the hydrogel, and into the right-hand limb, from which it evaporates.

In FIG. 4 the article is of cuboid shape. It has an internal partition wall 32 which extends from its top wall to a position approaching its bottom wall. However there is a space left between the bottom edge of the partition 32, and the bottom wall.

Water is present at the bottom of the article, and the water depth is such that the bottom edge of the partition wall is immersed in it. Above the water 34 to the right of the partition 32 is a first hydrophobic phase 36 comprising a first fragrance. Above the water 34 to the left of the partition is a second hydrophobic phase 38 comprising a second fragrance. A wick 40 has a major portion immersed in the first phase 36 and a minor portion exposed at the top of the article. The three phases are all coloured, differently.

A small vent hole 42 is provided in the top wall, to the left of the partition 32. The vent hole may be exposed on peeling off a sticker (not shown).

When the article of FIG. 4 is operational the first fragrance issues from the article first, by evaporation from the wick 40. After an interval, the second phase can start to bleed under the partition, and rise through the water. In this embodiment the first phase will not all have evaporated, when the second phase starts to bleed. The two fragrances are selected to be miscible, and to be olfactorily pleasant when blended; whereas the first and second phases are both immiscible with the water. It will be appreciated that once the second phase starts to bleed into the first phase there will form a composite fragrance, which will change as evaporation continues and bleeding of the second phase continues.

If wished a wick may be employed extending to the bottom of the right-hand chamber of the article, in order to obtain wick-assisted emanation throughout the life of the product.

In FIG. 5 the article is of cuboid shape. It has an internal partition wall 42 which extends from its top wall to its bottom wall. The partition wall 42 is made from a rigid impermeable plastics sheet material, except for a small section in contact with the bottom wall, this being a small plug 44 of a gel material which shrinks when in contact with air.

The partition wall 42 divides the article into two chambers. The right-hand or first chamber 46 contains a concentrated liquid fragrance 48. A wick 50 is provided, having a lower end adjacent to the bottom wall of the first chamber and an upper end standing exposed from the chamber. A small aperture 52 is provided in the upper wall of the first chamber. The wick is sufficiently rigid as to be self-supporting. Thus it comprises a rigid body, typically a plastics rod, covered with a flock of fibrous material along which the liquid fragrance may wick.

The bottom wall of the first chamber has on its inside a small circular wall 54, thereby forming a small pocket or well to receive the lower end of the wick. The wall 54 is directly beneath the hole 52 and so these parts keep the rigid wick in the desired upright location.

The left-hand or second chamber 56 contains a second, different, liquid fragrance. A small vent hole 58 is provided in the top wall of this chamber. The vent hole is exposed on removing a plastics plug (not shown).

When the article of FIG. 5 is operational the first fragrance issues from the article first, by evaporation from the wick 50. This continues until the evaporation of the first fragrance is complete, or nearly so. To be precise, it continues until the plug 44 which forms part of the partition 42 between the chambers is exposed to air. From that point the plug 44 starts to shrink. Depending on the effect required the gel material of the plug can be selected to shrink quickly and allow the second fragrance to burst past it and into the first chamber, while a small amount of the first fragrance remains; or to shrink slowly, so that by the time the second fragrance burst past the plug 44, the first fragrance has been exhausted.

Once the plug 44 is breached the second fragrance floods into the first chamber, until the liquid levels in the first and second chambers are the same. Evaporation via the wick 50 now continues, until the article is entirely exhausted.

In the article of FIG. 6 the article is U-shaped in cross-section, having a first upright limb 60, a second upright limb 62 and a horizontal connection limb 64. Thus the shape is of a somewhat squared-off U in cross-section (in contrast to the curved U-shape of the FIG. 3 embodiment).

The article of FIG. 6 has a depth several times lager than the limb width shown in FIG. 6, such that it is stable against toppling when it is placed on a flat horizontal surface.

The limb 60 is open at the top. It contains an evaporable gel 70, comprising a first fragrance. The limb 62 contains a liquid 68, comprising a second fragrance. Phases 60, 68 are kept apart by a gel 70 in the horizontal limb 64. The gel is of a type which shrinks when exposed to air.

The connecting limb 64 has at its uppermost surface a liquid-impermeable gas-permeable membrane 72 and, covering that membrane 72, a gas-and-liquid-impermeable barrier membrane 74, in the form of a peel-off sticker.

As with the other embodiments, the second limb is closed at its upper end except for a small vent hole 76 which in this embodiment is selectively opened and closed by a liftable/lowerable cover piece 78.

To use the article of FIG. 6, a foil seal (not shown) is first removed from the upper end of the first limb. The fragranced gel 66 slowly evaporates. Once the gel 66 has gone the barrier gel 70 in the connecting limb 64 is exposed to air and it shrinks back, progressively along its upper surface, until there is a passage for the liquid 68 to flow, over the shrunken gel, into the limb 60. As the liquid 68 evaporates from the limb 60, further liquid 68 flows to the limb 60, as the liquid levels continually equilibrate, until all of the liquid 68 has evaporated.

If the consumer wishes to accelerate the evaporation of the liquid 68 and/or to procure a mixed fragrance they can remove the sticker 74, exposing the gas-permeable membrane 72. The gel 70 is now exposed to air via the membrane 72 and will shrink back. Again, it will happen that there forms a passage for liquid 68 to flow from the second limb 62 to the first limb 60. The gel 66 in the first limb 60 is such that it can be impregnated by the liquid fragrance 68, by capillary action.

The invention claimed is:

1. An article for the release of a plurality of vapours, the article containing: a first liquid or gel phase comprising a first vaporisable agent; a second liquid or gel phase comprising a second vaporisable agent; and a third phase which is a gel whose volume reduces when exposed to air and which constitutes a barrier between the first and second phases; wherein the first and second phases are such that if placed in contact with each other one phase or one or more component thereof would mix or migrate into the other phase wherein the article comprises an enclosure having an internal partition wall which extends from a top wall to a bottom wall of the enclosure between the first phase and the second phase at the commencement of use of the article, the internal partition wall having a section not in contact with the bottom wall filled with a plug of said third phase gel; wherein, in use, initial vaporization of the first phase commences and when the first phase has substantially completely-issued from the article in use, the third phase is exposed to the air and can shrink, and wherein the third phase is configured to shrink slowly only to permit vaporization of the second phase once the first phase has been exhausted.

2. An article according to claim 1, wherein the first phase is a liquid.

3. An article according to claim 1, wherein the first phase is a gel.

4. An article according to claim 1, wherein the second phase is a liquid.

5. An article according to claim 1, wherein the second phase is a gel.

6. An article according to claim 1, wherein at least one of the first and second phases comprises as an evaporable agent a fragrance.

7. An article according to claim 1 wherein at least one of the first and second phases comprises as an evaporable agent a compound selected from an insecticide, insect repellent, miticide or anti-allergenic compound.

8. An article according to claim 1, where the third phase comprises a third evaporable agent.

9. A method of dispensing at least two active agents, using an article according to claim 1, wherein the commencement of evaporation of the first evaporable agent precedes the commencement of evaporation of the second evaporable agent, wherein initially vaporization of the first agent commences, and subsequently when the first phase has substantially completely issued from the article in use, the third phase is exposed to the air and can shrink, and wherein the third phase is configured to shrink slowly to only permit vaporization of the second phase once the first phase has substantially completely issued from the article.

* * * * *